United States Patent [19]

Alvila et al.

[11] Patent Number: 5,124,294
[45] Date of Patent: Jun. 23, 1992

[54] CATALYST SYSTEM AND PROCESS FOR PRODUCING ALCOHOLS FROM OLEFINES AND SYNTHESIS GASES

[75] Inventors: Leila Alvila; Tapani Pakkanen, both of Joensuu; Outi Krause; Matteus Joutsimo, both of Helsinki, all of Finland

[73] Assignee: Neste Oy, Finland

[21] Appl. No.: 133,042

[22] Filed: Aug. 25, 1987

[30] Foreign Application Priority Data

Dec. 27, 1985 [FI] Finland .................................. 855157
Dec. 22, 1986 [WO] PCT Int'l Appl. ... PCT/FI86/00155

[51] Int. Cl.$^5$ .............................................. C07C 29/16
[52] U.S. Cl. ...................... 502/62; 502/161; 502/166; 502/167
[58] Field of Search ................... 502/62, 161, 166, 167

[56] References Cited

U.S. PATENT DOCUMENTS 4,144,191 3/1979 Hartwell et al. ..................... 252/428
4,438,287 3/1984 Imai ..................................... 568/909

FOREIGN PATENT DOCUMENTS 2357645 12/1974 Fed. Rep. of Germany .

OTHER PUBLICATIONS

Chemical Abstracts, vol. 91 (1979), Abstract No. 157273t.
Chemical Abstracts, vol. 94 (1981), Abstract No. 139208h.
Chemical Abstracts, vol. 92 (1980), Abstract No. 110280y.

*Primary Examiner*—Patrick P. Garvin
*Assistant Examiner*—Brent M. Peebles
*Attorney, Agent, or Firm*—Steinberg & Raskin

[57] ABSTRACT

The present invention concerns a catalyst system and a process for selectively producing alcohols from olefines and synthesis gas. The catalyst system comprises one or several metal cluster compounds belonging to the cobalt group on an inorganic carrier and an amine of the form $NR_1R_2R_3$, where $R_1, R_2$ and $R_3$ are either hydrogen or an aliphatic or aromatic group containing 1 to 8 carbon atoms.

7 Claims, No Drawings

CATALYST SYSTEM AND PROCESS FOR PRODUCING ALCOHOLS FROM OLEFINES AND SYNTHESIS GASES

Applicants claim the benefit of PCT Application No. PCT/FI86/00155, filed Dec. 22, 1986, and through said application of Finnish Patent Application Ser. No. 855157, filed Dec. 27, 1985.

The present invention concerns a catalyst system and process by the aid of which alcohol can be produced from olefines and synthesis gases ($H_2 + CO$). This synthesis belongs to the group of hydroformylation, or oxo, reactions, by which compounds containing oxygen, such as aldehydes and alcohols, are usually produced from olefines. The catalysts to be used in the reaction are typically homogeneous and they contain rhodium or cobalt either in the form of carbonyls or phosphines. However, isolation of the catalyst dissolved in the reaction mixture poses a difficult problem, particularly when catalysts containing rhodium are used, and it affects the process costs. Endeavours have been made to avoid the drawbacks of homogeneous catalysis by binding the metal compounds on a solid carrier, which may be of organic or inorganic origin. However, heterogeneous hydroformylation catalysts are often less active than homogeneous ones, the metals are solved off the carriers in reaction conditions, and their thermal durability is limited.

Metal cluster compounds constitute a group of compounds which have favourable properties as catalyst precursors. In the U.S. Pat. No. 4,144,191, a bimetallic carbonyl cluster compound catalyst for producing alcohols by hydroformylation is disclosed. For cluster compound, either $Rh_2Co_2(CO)_{12}$ or $Rh_3Co(CO)_{12}$ is used, bound to an organic polymer containing amine groups. The catalyst operates at low temperature and produces almost exclusively alcohols.

In the Finnish patent application No. 844634 the observation is made that a mixture of the monometal cluster compounds $Rh_4(CO)_{12}$ and $Co_4(CO)_{12}$ bound to an amine resin carrier serves as the extremely selective catalyst in producing alcohols. An advantage of the cluster mixture catalyst is that it is simpler to prepare and its activity can be optimized as a function of the mole proportion of the metals.

Increasing the reaction rate in the hydroformylation reaction would be desirable, and feasible by raising the reaction temperature, but the thermal sensitivity of amine resin carriers restricts the raising of the reaction temperature. When using inorganic carrier materials, the use of higher temperatures would be possible. It was noted, however, in attempts to use monometal cluster compound mixtures containing rhodium and cobalt, or bimetallic compounds containing rhodium and cobalt, on inorganic carriers that the hydroformylation reaction in fact produced aldehydes only.

The object of the present invention is a catalyst system in which the above-mentioned drawbacks are avoided and which thus enables alcohols to be produced with high selectivity and at relatively high temperatures. The catalyst system of the invention for producing alcohols selectively from olefines and synthesis gases is characterized in that it comprises one or several metal cluster compounds belonging to the cobalt group on an inorganic carrier and an amine of the form $NR_1R_2R_3$, where $R_1$, $R_2$ and $R_3$ are either hydrogen or an aliphatic or aromatic group containing 1 to 8 carbon atoms.

Adding amine either into the reaction mixture, on the carrier, or to both, is indispensable for achieving sufficient alcohol conversion. The bimetallic $Co_2Rh_2(CO)_{12}$ mixture as well as a mixture of monometal clusters $Co_4(CO)_{12}$ and $Rh_4(CO)_{12}$ bound to aluminium oxide or silicon dioxide-based carriers produce nothing but aldehydes if no amines are present.

The most efficient amines have turned out to be tertiary amines $NR_3$, where R is any aliphatic or aromatic group.

The characteristics of the catalyst of the invention are influenced by factors related both to production technology and reaction technique. The catalyst is prepared by mixing a carrier and a metal cluster compound in a solvent. After the binding process has been completed, the solvent is removed, the catalyst rinsed with pure solvent, and dried in vacuum. The binding depends on the oxide carrier, on the chemical and mechanical characteristics. Aluminium oxide is one of the best agents for binding cobalt and rhodium compounds. Binding can also be observed on silicon oxide, zeolites and several silicates, for instance magnesium silicate. The binding efficiency of the carrier is also affected by its degree of grinding. The most finely ground carriers bind best, and they are also the most active in catalytic reactions. In practice, more coarsely ground materials are easier to handle.

Impregnating a tertiary amine directly into the carrier material prior to binding the cluster compound also results in an active hydroformylation catalyst producing alcohols. Admittedly, amine-impregnated aluminium oxide and silicon oxide bind cluster compounds less well, the consequence being that greater catalyst quantities have to be used.

The amine may also be added, not to the carrier, but directly to the reaction mixture, or part of the amine may be added to the reaction mixture and part of it to the catalyst. The quantity of amine is advantageously 0.1 to 10% by weight of the reaction mixture.

Secondary and primary amines also act as factors catalyzing the hydroformylation reaction of rhodium-cobalt cluster compounds bound on a carrier into alcohols. For instance, the conversion of 1-hexylene on adding diethylamine, $Et_2NH$, is certainly complete, but $C_7$ alcohols are produced, even in advantageous circumstances, only with about 70% selectivity. Moreover, the diethylamine is used up completely in hydroformamination with that 1-hexylene which is not converted into $C_7$ alcohols. It is thus noted that the metal compound catalyzes also this side reaction.

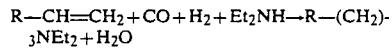

$$R-CH=CH_2 + CO + H_2 + Et_2NH \rightarrow R-(CH_2)_3NEt_2 + H_2O$$

Primary amines, such as aniline, behave in the same way and form the corresponding hydroformamination products. When the amine is replaced with ammonia in the hydroformylation mixture of 1-hexylene in the presence of $[Co_2Rh_2(CO)_{12}]$-aluminium oxide, the ability of the catalyst to produce $C_7$ products ceases altogether.

Adding a tertiary amine to the cluster catalyst mixture is not the only remarkable factor controlling the product distribution. The amount of the cluster compound on the carrier also exerts an influence on the activity and selectivity of the catalyst. Low metal content and longer reaction time result in more selective catalysis than a correspondingly larger catalyst quantity and shorter reaction time.

In producing the catalyst, either a mixed cluster compound $Co_xRh_{4-x}(CO)_{12}$, $x=1,2$ or 3, or a $Co_4(CO)_{12}$ and $Rh_4(CO)_{12}$ mixture can be used, without significant difference in catalytic characteristics in similar reaction conditions. In practice, the mixture is simpler and also enables the metal proportions to be optimized.

The performing of the hydroformylation reaction with the catalysts described in the foregoing is not significantly limited by external reaction conditions. Alcohol production takes place in the pressure range 1 to 7 MPa and in the temperature range 300 K. to 450 K. The composition of the catalyst and the reaction conditions may be optimized within these limits for a large group of starting material olefines.

EXAMPLE 1

The catalyst was prepared by mixing 1.0 g aluminium oxide (Alumina grades D, dried at 800° C.), 0.1 g $Co_2Rh_2(CO)_{12}$ (Martinego, S et al., J. Organomet. Chem. 59 (1973), p. 379) and 0.020 dm$^3$ hexylene in nitrogen atmosphere for 15 hrs. The hexylene containing unbound cluster material was removed. The catalyst was rinsed with hexylene and dried in vacuum.

EXAMPLES 2-4

The catalysts were prepared as in Example 1, except that in Example 2 the carrier was zeolite (Zeolon 900 Na), in Example 3 the carrier was a silicon dioxide (silika grades F 22), and in Example 4 the carrier was magnesium silicate.

EXAMPLE 5

The catalysts were prepared as in Example 1, except that the quantity of cluster compound $Co_2Rh_2(CO)_{12}$ was 0.05 g.

EXAMPLE 6

The catalyst was prepared as in Example 1, except that instead of the mixed cluster compound was used a cluster compound with 0.035 g $Co_4(CO)_{12}$ (Strem Chemicals), and 0.071 g $Rh_4(CO)_{12}$ (Martinego, S. et al, Inorganic Synthesis, Vol. 20, 1980, p. 209).

EXAMPLE 7

The catalyst was prepared as in Example 1, except that the aluminium oxide used for carrier was impregnated with 2 ml triethylamine (16 hrs). The excess was evaporated in vacuum.

EXAMPLE 8

The catalyst of Example 1 (0.1 g), 1-hexylene (1.0 dm$^3$), toluene (3.0 dm$^3$), and triethylamine $Et_3N$ (0.11 × 10$^{-3}$ dm$^3$, 0.79 mmol) were transferred in nitrogen atmosphere into an autoclave (V = 0.075 dm$^3$), into which 2.5 MPa $H_2$ and 2.5 MPa CO were added. The autoclave was kept at 373 K. for 17 hrs. The product mixture was cooled and analyzed with IR and NMR spectrometers, and by capillary gas chromatography. The reaction product contained 97% $C_7$ alcohols.

EXAMPLE 9

As Example 8, but the triethylamine quantity was 0.10 × 10$^{-3}$ dm$^3$. The reaction product contained 79% $C_7$ alcohols and 20% $C_7$ aldehydes.

EXAMPLE 10

As Example 8, but triethylamine quantity 0.05 × 10$^{-3}$ dm$^3$. The reaction product contained 30% $C_7$ alcohols and 55% $C_7$ aldehydes.

EXAMPLE 11

As Example 8, but triethylamine quantity 0.025 × 10$^{-3}$ dm$^3$. The reaction product contained 14% $C_7$ alcohols and 70% $C_7$ aldehydes.

EXAMPLE 12

As Example 8, but no amine was added. The reaction product contained 85% $C_7$ aldehydes.

Examples 9-12 show clearly that when the amount of amine is reduced in the catalyst system of the invention, the selectivity of alcohol forming deteriorates rapidly.

EXAMPLE 13

As Example 9, but the amine was $Et_2NH$ (0.79 mmol). The reaction product contained 62% $C_7$ alcohols and 19% $C_7$ aldehydes, and 19% byproducts containing amine.

EXAMPLE 14

As Example 8, but using the catalyst of Example 6 (0.353 g) and for alkene, propylene (0.8 g). The reaction mixture contained 90% $C_7$ alcohols.

EXAMPLE 15

As Example 8, but using the catalyst of Example 3 (0.1 g). The reaction mixture contained 56% $C_7$ alcohols and 39% $C_7$ aldehydes.

EXAMPLE 16

As Example 4, but using the catalyst of Example 5 (0.1 g). The reaction mixture contained 55% $C_7$ alcohols and 35% $C_7$ aldehydes.

EXAMPLE 17

As Example 8, but using the catalyst of Example 7 (0.1 g). The reaction mixture contained 70% $C_7$ alcohols, 16% $C_7$ aldehydes and 12% $C_{14}$ alcohols.

We claim:

1. A catalyst system for selectively producing alcohols from olefines and synthesis gases, comprising a mixture of metal cluster compounds $CO_4(CO)_{12}$ and $Rh_4(CO)_{12}$ or a mixed cluster compound of the formula $Co_xRh_{4-x}(CO)_{12}$, where $x = 1-3$, on an inorganic carrier and a tertiary amine of the form $NR_1R_2R_3$, where $R_1$, $R_2$ and $R_3$ are each an aliphatic or aromatic group containing 1 to 8 carbon atoms.

2. Catalyst system according to claim 1, characterized in that the amine has been added into the reaction mixture.

3. Catalyst system according to claim 1, characterized in that the amine has been added onto the inorganic carrier substance.

4. Catalyst system according to claim 1, characterized in that the amine quantity is 0.1 to 10% by weight of the quantity of the reaction mixture.

5. Catalyst system according to claim 1, characterized in that the amine is triethylamine.

6. Catalyst system according to claim 1, characterized in that the carrier substance is aluminium oxide, silicon dioxide, zeolite or magnesium silicate.

7. The catalyst system of claim 1, wherein said inorganic carrier is an inorganic oxide carrier.

* * * * *